United States Patent [19]

Haagen

[11] 4,122,389
[45] Oct. 24, 1978

[54] MOISTURE SENSOR

[75] Inventor: Peter H. Haagen, Arlington, Tex.

[73] Assignee: Tandy Corporation, Fort Worth, Tex.

[21] Appl. No.: 799,225

[22] Filed: May 23, 1977

[51] Int. Cl.$^2$ .............................................. G01R 27/02
[52] U.S. Cl. ..................... 324/65 R; 324/51;
324/133; 340/604; 340/378 R
[58] Field of Search .................. 324/65 R, 62, 64, 51,
324/133; 340/235, 324 R, 332, 378 R

[56] References Cited

U.S. PATENT DOCUMENTS

| | | | |
|---|---|---|---|
| 3,283,244 | 11/1966 | Proctor et al. | 324/62 R |
| 3,452,347 | 6/1969 | Stimson | 324/133 X |
| 3,513,393 | 5/1970 | Myers | 324/133 |
| 3,649,913 | 3/1972 | Flieder et al. | 324/133 |
| 3,828,256 | 8/1974 | Liu et al. | 324/133 |
| 3,964,039 | 6/1976 | Craford | 324/133 X |
| 3,979,667 | 9/1976 | Cornes | 324/65 R |
| 4,002,968 | 1/1977 | Reid | 324/51 |
| 4,006,409 | 2/1977 | Adams | 324/133 X |

Primary Examiner—Stanley T. Krawczewicz
Attorney, Agent, or Firm—Wolf, Greenfield & Sacks

[57] ABSTRACT

A soil moisture sensing device employs a pair of indicator lamps to indicate whether the soil is too dry, too wet, or has the correct amount of moisture. The device need employ only one transistor or one Darlington transistor pair to control both indicators. Consequently, the device is more economical to manufacture than "prior art" soil moisture sensing devices that must use two or more transistors. In the invention, too dry soil is indicated by non-conduction of the transistor with neither indicator illuminated, adequately moist soil is indicated by partial conduction with one indicator illuminated, and too wet soil is indicated by full conduction with both indicators illuminated.

12 Claims, 3 Drawing Figures

MOISTURE SENSOR

BACKGROUND OF THE INVENTION

The present invention relates in general to humidity sensors of the type having a probe that is inserted into the soil and is concerned more particularly with an improved electrical circuit for indicating the moisture or humidity condition of the soil. The invention has its preferred application in monitoring soil for plants to enable the humidity of the soil to be kept at a level that is proper for the plants.

The proper watering of house plants is not easily accomplished and many times the plants are over-watered or under-watered. The difficulty is due to the many different variables that affect the moisture content of the soil in which the plant is disposed. For example, in the case of potted plants in a house, soil moisture can be affected by the size of the pot, the relative humidity of the air in the room, the type of soil used, and the amount of light the plant receives. "Prior art" soil moisture indicators such as the one shown in U.S. Pat. No. 3,979,667 employ a probe having two terminals for sensing the resistance of the soil to current flow between the terminals. Although such devices function adequately as indicators, their manufacturing cost tends to be somewhat high because they require at least two separate transistors and associated biasing resistors.

Accordingly, the principal object of the present invention is to provide a low cost soil moisture indicator that uses fewer components than "prior art" indicator devices and whose performance is as good as or better than the performance of the "prior art" devices.

SUMMARY OF THE INVENTION

To accomplish the foregoing object of this invention there is provided, in combination with the probe, a circuit having a pair of indicator lamps capable of indicating at least three different conditions of moisture or humidity of the soil being sensed. In the preferred embodiment these indicators are light emitting diodes. The circuit employs a transistor, or in one alternate embodiment a Darlington transistor pair. The transistor includes an input or control electrode which couples to a voltage divider network which in turn couples to one terminal of the probe. The transistor further includes output or main electrodes which couple, respectively, to the light emitting diodes. A series connection of a resistor and light emitting diode connect at one of the output electrodes while a parallel combination of a resistor and light emitting diode connect at the other output electrode. A DC battery is preferably used as the power source and provides power to the circuit and probe of this invention.

When the probe is inserted into too dry soil, the high resistance of the soil causes the transistor to be held in the non-conductive or slightly conductive state where neither of the two indicators is illuminated. When the soil has a somewhat moist condition the resistance of the soil is reduced and causes the transistor to conduct to the extent which enables the series connected light emitting diode to be lit. When the soil is too wet, the soil resistance is at its lowest level and the transistor is at a higher level of conduction, causing illumination of both the series and parallel connected light emitting diodes.

BRIEF DESCRIPTION OF THE DRAWINGS

The invention, both as to its construction and mode of operation, can be better understood from the detailed description which follows when considered in conjunction with the accompanying drawings, in which.

DETAILED DESCRIPTION OF PREFERRED EMBODIMENTS

Figure 1:
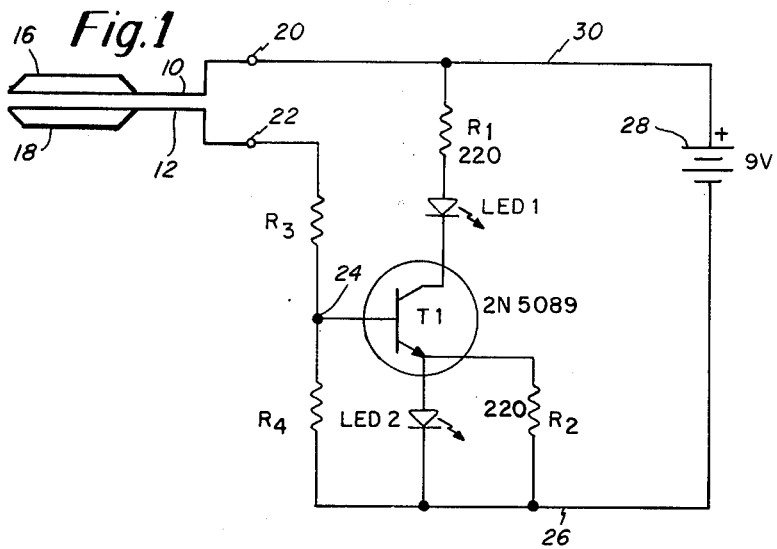
FIG. 1 is a diagram of a one transistor circuit arranged in accordance with the invention.

In the drawings like reference characters are used to identify like circuit components. FIG. 1 shows a circuit arranged in accordance with the invention and having leads 10 and 12 extending from the electrodes of probe. This probe includes electrodes 16 and 18 which connect respectively to leads 10 and 12. The other end of the leads 10 and 12 connect to the terminals 20 and 22, respectively. A similar probe is used in connection with the circuits of FIGS. 2 and 3 connecting similarly to the terminals 20 and 22. It is the resistance of the soil bridging electrodes 16 and 18 that is monitored to determine the moisture content therein.

The embodiment of FIG. 1 comprises a single transistor T1 having a base electrode, a collector electrode and an emitter electrode. The base electrode or control electrode couples to node 24 of the voltage divider network including resistors R3 and R4. This voltage divider network couples between terminal 22 and ground or negative voltage line 26 which is maintained at a negative or ground potential by being connected to the battery 28. The other terminal 20 couples directly by way of positive voltage line 30 to the positive terminal of battery 28. Battery 28 is preferably a 9 volt battery or a bank of 9 volt batteries.

The resistance impressed across the terminals 20 and 22 sensed by the probe is in series with the voltage divider network comprising resistors R3 and R4. Thus, as the resistance across terminals 20 and 22 changes so also does the voltage at the node 24. At higher resistance values the voltage at node 24 is at a lower voltage, and when the resistance across terminals 20 and 22 is at a lower resistance value, the voltage at node 24 increases.

Figure 2:
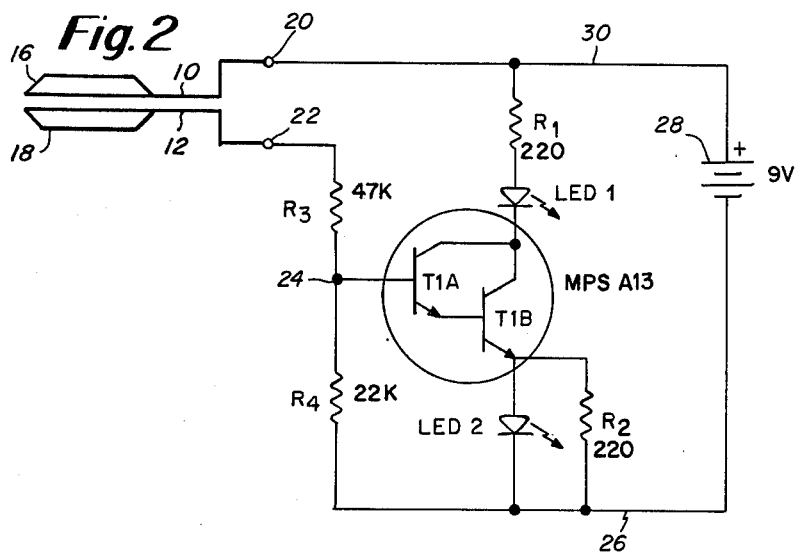
FIG. 2 shows a modification of the FIG. 1 circuit in which the transistor is replaced by a Darlington pair.
Figure 3:
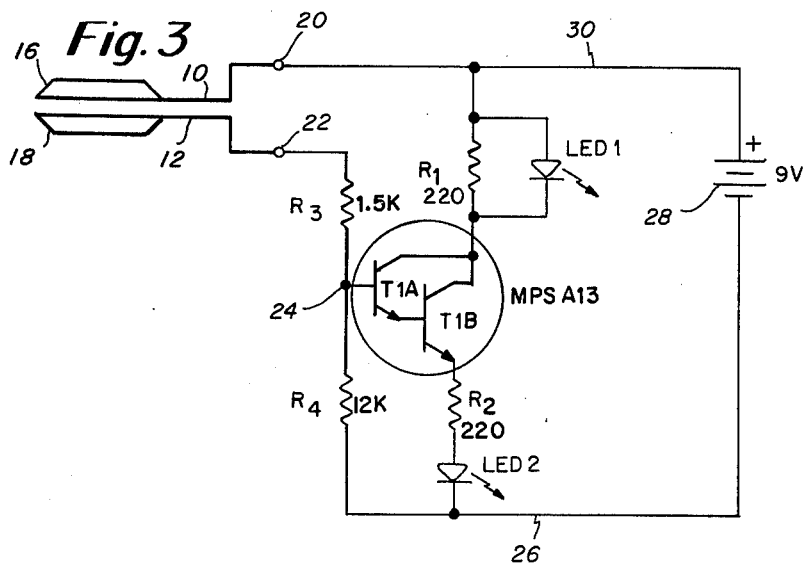
FIG. 3 is a diagram showing the circuit arrangement deemed by the inventor to be the best mode of carrying out his invention.

The value of resistors R3 and R4 depend upon at least three different factors. Typical values for these resistors are shown in the embodiments of FIGS. 2 and 3. The selection of these resistors depend upon whether a single transistor is being used as in the embodiment of FIG. 1 or whether a Darlington transistor is used as shown in FIGS. 2 and 3. The value of resistors R3 and R4 is also a function of the battery voltage that is selected. The value of resistors R3 and R4 also depends upon the size, shape and separation of the exposed electrodes 16 and 18. Furthermore, the values of resistors R3 and R4 depend upon the particular threshholds that are selected for the dry, moist and wet conditions.

The collector of transistor T1 couples to the series connection of light emitting diode LED1 and resistor R1. This series circuit connects between the collector of transistor T1 and positive voltage line 30. The emitter of transistor T1 couples to a parallel circuit including light emitting diode LED2 and resistor R2. This parallel circuit connects between the emitter of transistor T1 and the ground or negative voltage line 26.

When the soil resistance as impressed across terminals 20 and 22 is high because the soil is dry then the voltage at node 24 is at its low level or near the voltage on line 26. Under this condition the transistor T1 is non-conductive and there is essentially no current flow between the emitter and collector of transistor T1. There is also thus no current flow through the series or parallel circuits and the light emitting diodes LED1 and LED2 are not illuminated.

When the soil is in a moist condition the resistance across terminals 20 and 22 is at a lower value and the voltage at node 24 increases from its lower voltage level when the soil was dry. Under this condition there is a partial conduction of transistor T1 sufficient to cause illumination of the light emitting diode LED1. The partial conduction of transistor T1 does not illuminate LED2 as the current is essentially by-passed by way of resistor R2 at these low current levels. The LED2 preferably has a "red" illumination and requires typically 1.6 volts across its terminals before it will be turned on. As long as the current through resistor R2 is insufficient to cause a 1.6 volt drop across resistor R2, then the LED2 remains off. With the typical value of 1.6 volts and a value of resistor R2 of 220 ohms then the threshold current is on the order of 7.3 milliamps.

When the soil is wet the voltage at node 24 is at its highest level in comparison to the other soil conditions and thus transistor T1 may be in full conduction. Under this condition both LED1 and LED2 are illuminated since the current flow through transistor T1 and resistor R2 is sufficient to cause LED2 to conduct. LED1 is brighter in its level of conduction because part of the current going to LED2 is by-passed by resistor R2.

The embodiment of FIG. 2 operates in substantially the same manner as discussed previously with the operation of the circuit of FIG. 1. The basic difference between the circuit of FIG. 2 and the circuit of FIG. 1 is that a Darlington transistor is used in FIG. 2 to provide sufficient gain. In FIG. 1 the transistor T1 is preferably a high gain transistor so as to provide the necessary currents for the indicators. The Darlington transistor shown in FIG. 2 is readily available on a single chip and the price thereof varies very little from the price of a single transistor.

FIG. 3 shows the preferred embodiment of the invention employing Darlington transistor T1A, T1B having its base electrode coupled to the voltage divider network comprising resistors R3 and R4. In the embodiment of FIG. 3 the series circuit comprising resistor R2 and LED2 is coupled to the emitter of transistor T1B and the parallel circuit comprising resistor R1 and LED1 is coupled to the collector of transistor T1B. With the embodiment of FIG. 3 for a dry soil condition the Darlington transistor is non-conductive and neither of the light emitting diodes is illuminated. For a moist soil condition the transistor is partially conductive and only LED2 is illuminated. For wetter soil conditions the transistor is more conductive and both light emitting diodes are then illuminated.

With regard to the circuit embodiment of FIG. 3 the LED2 may register a "green" indication while the LED1 may register a "red" condition. On the other hand the color indications are not absolutely necessary in that illumination of one diode indicates a moist condition while illumination of two diodes indicates a moist condition while illumination of two diodes indicates a wet condition. When the color indications are used a "green" indication alone denotes moist soil while a "red" and "green" denote soil that is overwatered.

Having described a limited number of embodiments of the present invention it should now become apparent to those skilled in the art that numerous other embodiments of the invention exist all of which are contemplated as falling within the scope of this invention as defined by the appended claims. For example, in the drawings, the device has been shown as battery-operated. In an alternative embodiment the device may operate from an AC source having its own built-in power supply to provide the DC voltage levels for the circuit. The circuits shown in FIGS. 1-3 show NPN transistors. In an alternative embodiment PNP type transistors may be used. In still another embodiment the Darlington transistor of FIG. 3 may be replaced by a single transistor as in FIG. 1.

What is claimed is:

1. A soil moisture indicator device for connection to a probe having electrodes across which the variable resistance of the soil is impressed, said device comprising; a transistor means having an input control electrode and a pair of output electrodes, means providing power to the circuit, means coupling one electrode of the probe to the control electrode of the transistor means to vary the conduction of the transistor means as a function of soil resistance, first light indicating means coupled in series with one output electrode of the transistor means and being illuminated upon at least a first partial conduction of said transistor means, and second light indicating means and resistor means connected in parallel and together coupled in series with the other output electrode of the transistor means, both said first and second light indicating means being illuminated upon conduction of said transistor means at a level of conduction greater than the first partial conduction level.

2. A soil-moisture indicator device as set forth in claim 1 wherein said transistor means comprises a single transistor with the control electrode being the base, and the output electrodes being the emitter and collector of the transistor.

3. A soil-moisture indicator device as set forth in claim 2 wherein said means for providing power includes a battery and two DC voltage level lines, said first light indicating means coupling from the transistor to one of the lines and said second light indicating means coupling from the transistor to the other line.

4. A soil-moisture indicator device as set forth in claim 1 wherein said transistor means comprises a Darlington transistor.

5. A soil-moisture indicator device as set forth in claim 1 wherein said means for coupling includes a pair of resistors defining a voltage divider network in series with the probe electrodes and having a node coupling to the control electrode.

6. A soil-moisture indicator device as set forth in claim 1 wherein said first light indicating means includes a light emitting diode and resistor connected in series.

7. A soil-moisture indicator device as set forth in claim 6 wherein said second light indicating means includes a light emitting diode.

8. A soil-moisture indicator device as set forth in claim 7 wherein said first light indicating means is connected to the collector electrode and said second light indicating means is connected to the emitter electrode.

9. A soil-moisture indicator device as set forth in claim 7 wherein said first light indicating means is connected to the emitter electrode and said second light indicating means is connected to the collector electrode.

10. A soil-moisture indicator device as set forth in claim 3 wherein said first light indicating means coupled in series between said one output electrode and said one line and said second light indicating means couples in series between said other output electrode and said other line.

11. A soil-moisture indicator device as set forth in claim 10 wherein said first light indicating means is connected to only said one output electrode of said pair of output electrodes, and said second light indicating means is connected to only said other output electrode of said pair of output electrodes.

12. A soil-moisture indicator device as set forth in claim 11 wherein said first light indicating means includes a light emitting diode, said second light emitting diode includes a light emitting diode and said resistor means includes a resistor, and further including a series resistor in series with said first light emitting diode, said resistor in parallel with said second light emitting diode being for by-passing current from said second light emitting diode to prevent substantial illumination thereof at partial conduction of said transistor means.

* * * * *